United States Patent [19]

Williams

[11] Patent Number: 4,578,083
[45] Date of Patent: Mar. 25, 1986

[54] ARTIFICIAL LEG

[76] Inventor: Allton C. Williams, 5118 Longridge, Sherman Oaks, Calif. 91423

[21] Appl. No.: 495,149

[22] Filed: May 16, 1983

[51] Int. Cl.⁴ ............................................. A61F 1/02
[52] U.S. Cl. ...................................... 623/42; 623/43; 623/46
[58] Field of Search ...................................... 3/22–29, 3/2, 4, 6

[56] References Cited

U.S. PATENT DOCUMENTS 2,522,853  9/1950  Black ........................................ 3/27
2,570,581  10/1957  McIntyre .................................. 3/27

FOREIGN PATENT DOCUMENTS 1136136  5/1957  France ........................................ 3/2
113500  7/1918  United Kingdom ....................... 3/2
142338  5/1920  United Kingdom ..................... 3/26

Primary Examiner—Richard J. Apley
Assistant Examiner—David J. Isabella
Attorney, Agent, or Firm—Sanford Astor

[57] ABSTRACT

This invention relates to an artificial leg comprising an elongated lower leg portion, an ankle joint, an upper portion adapted to strap to the wearer's thigh, a knee joint comprising an upper and lower cam, the upper cam adapted to rotate around a pivot and having a convex shape and a lower cam having a concave shape and an elongated arm portion which locks into the upper cam when pressure is placed on the leg and releases by spring action when pressure is released from the leg.

4 Claims, 3 Drawing Figures

ARTIFICIAL LEG

BACKGROUND OF THE INVENTION

This invention relates, in general, to artificial limbs and particularly to an artificial leg. Many devices have been made in the past which are used as a substitute for an amputated leg. Some of these artificial limbs, while reasonably satisfactory, have been too complex in a mechanical sense so that they have been very difficult for the user. This is particularly true when repairs are necessary. Many existing artificial limbs have been difficult to manipulate by the person using them. One of the biggest problems encountered has been the need for a knee joint action which will lock, so that the user can go up and down stairs in a normal manner.

OBJECTS OF THE INVENTION

It is an object of this invention to provide an artificial leg with a knee joint action that allows the user to make normal steps with the leg.

Still a further object of the invention is to provide an artificial limb in which the knee joint action is smooth acting and gives great stability to the wearer.

Still a further object of the invention is to provide an artificial limb with a mechanical knee device which functions as close to a real knee joint action as possible, and allows the wearer to walk naturally with positive control of his movements.

DESCRIPTION OF THE INVENTION

The above objects and advantages of the invention will become apparent upon reference to the accompanying drawings in which FIG. 1 is a side view partially broken away of the device of the present invention.

Figure 1:
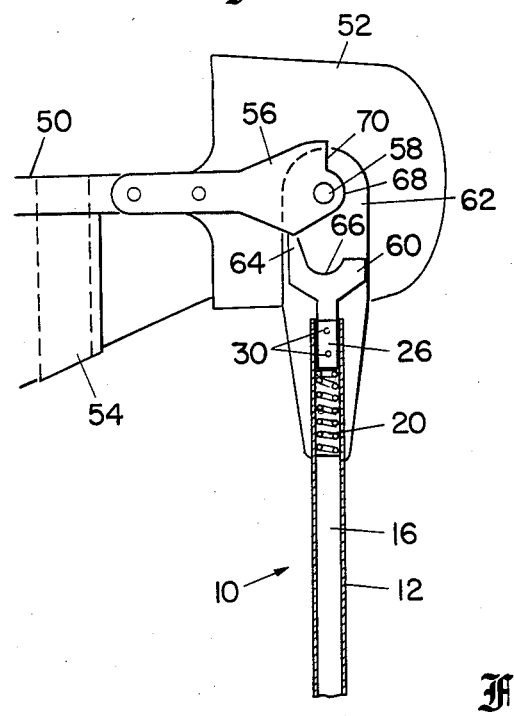
Figure 2:
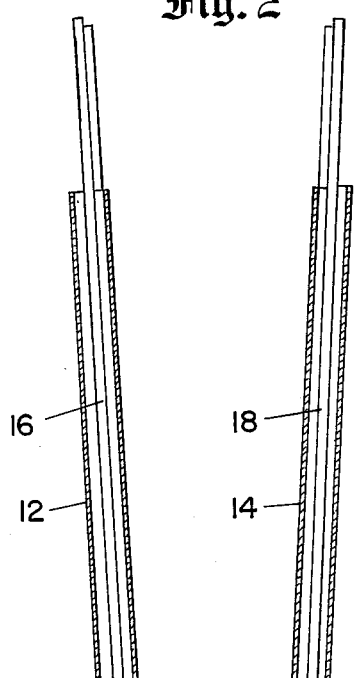
FIG. 2 is a front view of the device of the present invention.

Referring now to FIG. 1 and FIG. 2 there is shown a device 10 of the present invention comprising a pair of elongated tubular rods or sleeves 12 and 14, more clearly shown in FIG. 2. Inside of each tubular rod 12 and 14 is a solid rod 16 and 18, which fit inside the tubular sleeves or rods 12 and 14. At each end of the solid rods 16 and 18 is a compression spring 20 and 22. These springs rest against a lower guide 24 and an upper guide 26. These guides are kept in position and kept from rotating by set screws 28 and 30. These elements form the lower leg extended portion of the artificial limb of the present invention.

The ankle portion of the device of the present invention comprises a well known "Klenzak" ankle joint 32 and 34. The "Klenzak" ankle joint comprises a ball bearing 36 to which is attached a spring 38 inside of an outer shell 40. A screw 42 is utilized to adjust the pressure of the spring 38. The object of the "Klenzak" ankle joint is that when the person lifts the artificial leg to take a step, the shoe 44, which is held by brackets 46, 48, is rotated in a toe upward direction so that the toe will not be stubbed as the person takes a step. This joint is well known in the art.

The upper or knee portion of the device of the present invention is the portion of the device of the present invention which is the key to the improved action of this device. This upper knee portion, together with the springs in the lower leg portion, as will be explained, operate to allow the user to take a normal step and to go up and down stairs because of the locking action and unlocking action of the knee joint.

The upper portion of the device of the present invention comprises an upper vertical rod 50, a cup 52 into which the stump of the leg is placed, and leather bindings 54 or other means to tie the leg, with the stump in the cup 54, to the person using the device.

The knee action takes place by an upper cam 56 fixedly attached to rod 50, adapted to rotate around a pivot pin 58 and fit into a lower cam 60. The lower cam 60 is attached to the lower vertical leg 12. There are two such cam actions, one on each of the two struts on either side of the knee portion of the device of the present invention. There are two lower cams 60 attached to the lower verticals 12 and 14. These lower verticals are adjustable in length by any convenient method, such as a screw adjustment. The upper ends of the tubes 12 and 14 are secured to a hinge plate 62, such as by welding. If desired a plastic calf shell can be added surrounding the device at the lower verticals and if desired a cover plate can cover the knee portion so that clothing will not get caught in the knee joint.

The unique action of the knee joint of the present invention takes place because the lower cam 60 has elongated rear arm portion 64 creating a concave cup 66 in the center of the cam 60. The upper cam 56 has a corresponding central convex shape 68, and a stopping plate 70 so that when the user rotates the knee in a forward direction so that the user's weight is applied on the lower vertical 12, 14, the lower verticals 12, 14 raise up due to the spring action 20, 22 and engage the upper cam 56 using the convex 68 to the concave portion 66, and the stopping arms 64 and 70 have locked into place, so that the user can put his full weight onto the device. When the user removes his weight by placing his weight onto the other or good leg, the lower cam 60 disengages due to the spring action 20, 22 pulling the lower vertical 12, 14 in a downward direction and allows the knee joint to bend. When the next step is taken, and weight is again put on to the leg by the foot against the pavement, the spring action again rotates the cam and locks it into position so that weight can be put on to the knee joint.

Figure 3:
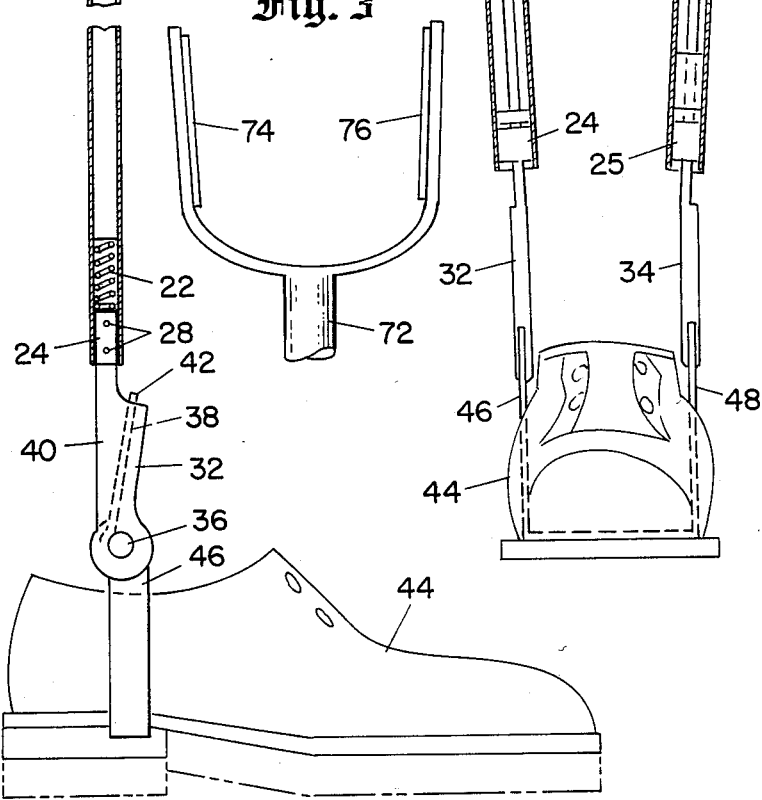
FIG. 3 is a partial view of another embodiment of the lower portion of the device of the present invention.

FIG. 3 simply shows another embodiment of the device of the present invention in which the lower vertical, rather than being two elongated rods, is a single elongated rod 72 up to just below the knee portion where it separates into two rods 74 and 76, in a U-shaped manner, to provide the arms which have the same cam action as described in FIGS. 1 and 2.

The construction of the orthopedic appliance of the present invention shows a relatively simple mechanical device which requires a minimum of maintenance and yet provides a locking action that does not exist except in very complex form in presently known devices. The locking cam action of the device of this invention, as stated, allows the user to take a normal step, be assured that his knee will lock, and support him so that he can put full weight on the artificial limb. Again, this is due to the spring action in the lower limb allowing the cam portion of the knee to engage and dis-engage as weight is placed or released on the artificial limb.

Having thus described the invention, it is requested that the invention be limited only by the scope of the attached claims.

I claim:

1. An artificial leg comprising an elongated lower leg portion comprising a tubular sleeve having therein a rod and springs means fixedly attached to each end of said rod within said sleeve, an ankle joint having one end attached to a shoe and an opposite end attached to a lower end of said rod;

an upper leg portion, means to attach said upper leg portion to the thigh of the wearer;

a knee joint located at an upper end of said rod comprising an upper cam and a lower cam, said upper cam is attached to said upper leg portion and adapted to rotate about a pivot, said upper cam having a convex surface defined by a semi-circle wherein a flat surface extending forward of said surface is substantially perpendicular to the tangent of said circle and a rearwardly extending surface is substantially parallel to the tangent of said circle; and said lower cam is attached to the said upper portion of said rod and having a concave surface and an elongated rearwardly extending finger and a planar surface extending in a forward direction wherein each of said surfaces of the lower cam compliment said upper cam surfaces so as to lock with said upper cam when pressure is placed on the leg and wherein said springs maintain constant friction between said upper cam and lower cam.

2. The device of claim 1 comprising two lower leg portions and two upper leg portion, said lower leg portions adapted to attach to both sides of a shoe.

3. The device of claim 1 comprising one lower leg portion and two upper leg portions, said lower leg portions dividing to a U-shaped knee portion.

4. The device of claim 1 in which the lower leg portion and knee portion are covered by a plastic cover simulating a calf and knee.

* * * * *